US009097658B2

(12) United States Patent
Afzali-Ardakani et al.

(10) Patent No.: US 9,097,658 B2
(45) Date of Patent: Aug. 4, 2015

(54) CARBON BASED BIOSENSORS AND PROCESSES OF MANUFACTURING THE SAME

(71) Applicant: International Business Machines Corporation, Armonk, NY (US)

(72) Inventors: Ali Afzali-Ardakani, Ossining, NY (US); Shu-Jen Han, Cortlandt Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 386 days.

(21) Appl. No.: 13/706,784

(22) Filed: Dec. 6, 2012

(65) Prior Publication Data

US 2014/0158551 A1    Jun. 12, 2014

(51) Int. Cl.
     *G01N 33/543*    (2006.01)
     *G01N 27/414*    (2006.01)
     *H01L 51/00*    (2006.01)
     *B82Y 10/00*    (2011.01)
     *B82Y 15/00*    (2011.01)
     *G01N 33/551*    (2006.01)
     *H01L 51/05*    (2006.01)
     *B82Y 40/00*    (2011.01)

(52) U.S. Cl.
     CPC ............ *G01N 27/4146* (2013.01); *B82Y 10/00* (2013.01); *B82Y 15/00* (2013.01); *G01N 33/5438* (2013.01); *G01N 33/551* (2013.01); *H01L 51/0045* (2013.01); *H01L 51/0048* (2013.01); *H01L 51/0067* (2013.01); *H01L 51/0072* (2013.01); *H01L 51/0558* (2013.01); *B82Y 40/00* (2013.01)

(58) Field of Classification Search
     CPC ............ G01N 27/414; G01N 27/4145; G01N 27/4146; G01N 33/553; G01N 33/5438; H01L 51/0002; H01L 51/0045; H01L 51/0048; H01L 51/0072; H01L 51/0558; B82Y 5/00

See application file for complete search history.

(56) References Cited

U.S. PATENT DOCUMENTS 8,138,102 B2    3/2012    Afzali-Ardakani et al.

FOREIGN PATENT DOCUMENTS

| WO | 2009158117 A2 | 12/2009 |
| WO | 2010144157 A1 | 12/2010 |
| WO | 2011011828 A1 | 2/2011 |

OTHER PUBLICATIONS

Y. Ohno, K. Maehashi, K. Matsumoto, Graphene Field-Effect Transistors for Label-Free Biological Sensors, IEEE Sensors 2010 Conference, pp. 903-906 (2010).*
Y. Ouyang, H. Dai, J. Gao, Projected Performance Advantage of Multilayer Graphene Nanoribbons as a Transistor Channel Material, Nano Res, vol. 3, pp. 8-15 (2010).*

(Continued)

*Primary Examiner* — J. Christopher Ball
*Assistant Examiner* — Maris R Kessel
(74) *Attorney, Agent, or Firm* — Cantor Colburn LLP; Vazken Alexanian

(57) ABSTRACT

Sensors, processes for manufacturing the sensors, and processes of detecting a target molecule with the sensor generally includes a substrate including a channel and first and second electrodes electrically connected to the channel, wherein the channel includes a monolayer of surface functionalized graphene or surface functionalized carbon nanotubes, wherein the surface functionalized graphene or surface functionalized carbon nanotubes include an imidazolidone compound.

14 Claims, 3 Drawing Sheets

(56) References Cited

OTHER PUBLICATIONS

Ariga, Katsuhiko., et al. "By What Means Should Nanoscaled Materials Be Contructed: Molecule, Medium, or Human?", Nanoscale., vol. 2, pp. 198-214, (2010).
Kasry, Amal., et al. "Detection of Biomolecules via Benign Surface Modification of Graphene", Chem. Mater., vol. 23, pp. 4879-4881, (2011).
Kasry, Amal., et al. "Highly Efficient Fluorescence Quenching with Graphene", J. Phys. Chem., vol. 116, pp. 2858-2862, (2012).
Sabri, S.S., et al. "Graphene Field Effect Transistors with Parylene Gate Dielectric", Applied Physics Letters, vol. 95, pp. 242104-1 through 242104-3, (1995).
Zhou, Bao H., et al. "X-Ray Structures and Binding Properties of Molecular Clips Based on Diethoxycarbonyl Glycoluril", Can. J. Chem., vol. 85, pp. 586-591, (2007).

* cited by examiner

CARBON BASED BIOSENSORS AND PROCESSES OF MANUFACTURING THE SAME

BACKGROUND

The present disclosure is generally directed to biosensors including channels of functionalized graphene or functionalized carbon nanotube surfaces configured to immobilize to the surface analytes such as metal particles, polymers, organic molecules, macromolecules and particularly of biological molecules chosen from peptides, polypeptides, proteins such as enzymes, nucleic acids, antibodies or antibody fragments, polysaccharides, cells and cell fragments.

Graphene and carbon nanotubes (CNTs) have attracted attention in the field of sensing due to their exceptional charge transport characteristics, which are generally confined to the surface and are able to detect molecular level changes in their immediate environment since these materials. Ever since the first demonstration of CNT sensing capability on gas molecules, numerous studies have reported on the interaction of CNTs with a variety of biological and bioactive species such as proteins, peptides, DNA, enzymes, and the ability to transduce this interaction into an effective sensor. By virtue of their small size, the sensitivity of the detecting or sensing elements such as nanotubes and nanowires, and the versatility to detect specific bindings of a vast group of analyte: analyte-binding molecules, nanostructure-based biosensors are rapidly gaining employability in real-time detection of the presence of biological molecules. For instance, single-walled carbon nanotubes (SWCNTs) have been employed in the detection of deoxyribonucleic acid (DNA) based on both electrochemical and transistor configuration and detection limits of the order of parts per trillion have been reported.

Graphene is generally described as an open nanotube of a two-dimensional planar sheet of carbon atoms arranged in a hexagonal benzene-ring structure. A free-standing graphene structure is theoretically stable only in a two-dimensional space, which implies that a truly planar graphene structure does not exist in a three-dimensional space, being unstable with respect to formation of curved structures such as soot, fullerenes, nanotubes or buckled two dimensional structures. However, a two-dimensional graphene structure may be stable when supported on a substrate, for example, on the surface of a silicon carbide (SiC) crystal. Free standing graphene films have also been produced, but they may not have the idealized flat geometry.

Structurally, graphene has hybrid orbitals formed by sp2 hybridization. In the sp2 hybridization, the 2s orbital and two of the three 2p orbitals mix to form three sp2 orbitals. The one remaining p-orbital forms a pi ($\pi$)-bond between the carbon atoms. Similar to the structure of benzene, the structure of graphene has a conjugated ring of the p-orbitals, i.e., the graphene structure is aromatic. Unlike other allotropes of carbon such as diamond, amorphous carbon, carbon nano foam, or fullerenes, graphene is only one atomic layer thin.

Graphene has an unusual band structure in which conical electron and hole pockets meet only at the K-points of the Brillouin zone in momentum space. The energy of the charge carriers, i.e., electrons or holes, has a linear dependence on the momentum of the carriers. As a consequence, the carriers behave as relativistic Dirac-Fermions with a zero effective mass and are governed by Dirac's equation. Graphene sheets may have a large carrier mobility of greater than 200,000 cm2/V-sec at 4K. Even at 300K, the carrier mobility can be as high as 15,000 cm2/V-sec.

Graphene layers may be grown by solid-state graphitization, i.e., by sublimating silicon atoms from a surface of a silicon carbide crystal, such as the (0001) surface. At about 1,150° C., a complex pattern of surface reconstruction begins to appear at an initial stage of graphitization. Typically, a higher temperature is needed to form a graphene layer. Graphene layers on another material are also known in the art. For example, single or several layers of graphene may be formed on a metal surface, such as copper and nickel, by chemical deposition of carbon atoms from a carbon-rich precursor.

Graphene displays many other advantageous electrical properties such as electronic coherence at near room temperature and quantum interference effects. Ballistic transport properties in small scale structures are also expected in graphene layers.

While single-layer graphene sheet has a zero band-gap with linear energy-momentum relation for carriers, two-layer graphene, i.e. bi-layer graphene, exhibits drastically different electronic properties, in which a band gap may be created under special conditions. In a bi-layer graphene, two graphene sheets are stacked on each other with a normal stacking distance of roughly 3.35 angstrom, and the second layer is rotated with respect to the first layer by 60 degree. This stacking structure is the so-called A-B Bernel stacking, and is also the graphene structure found in natural graphite. Similar to single-layer graphene, bi-layer graphene has zero-band gap in its natural state. However, by subjecting the bi-layer graphene to an electric field, a charge imbalance can be induced between the two layers, and this will lead to a different band structure with a band gap proportional to the charge imbalance.

Because of the unique electric properties associated with carbon nanotubes and graphene, these materials are attractive for applications in nanotechnology. Semiconducting carbon nanotubes, in particular, have received attention, due to their promising performance in electronic devices, such as diodes and transistors. For example, carbon nanotubes and graphene can be used as channels in field effect transistors (FETs). The most common prior art method of fabricating carbon nanotube FETs starts with depositing a carbon nanotube on a thin oxide film from a liquid suspension. Source and drain contacts are then formed lithographically on the nanotube to form a FET device.

The deposition of carbon nanotubes on an oxide surface, followed by lithographic patterning of the source and drain contacts, has been successfully used in the prior art for the construction of single carbon nanotube FETs. However, fabrication of integrated circuits from nanotubes requires the precise placement and alignment of large numbers of carbon nanotubes on a surface (e.g., spanning the source and drain contacts). E. Valentin, et al., "High-density selective placement methods for carbon nanotubes", Microelectronic Engineering, 61-62 (2002), pp. 491-496 disclose a method in which the adhesion of carbon nanotubes onto a $SiO_2$ surface is improved using aminopropyltriethoxysilane (APTS). In this prior art, APTS is employed to form a silanized surface on $SiO_2$, which is then used to selectively place the carbon nanotubes.

A drawback with the prior art process disclosed in the E. Valentin, et al. article is that the trialkoxysilane undergoes polymerization in solution and self-assembly must be carried out under controlled conditions excluding water. Additionally, APTS cannot be printed using conventional poly(dimethylsiloxane) (PDMS) stamps in contact printing because the solvents that are used for APTS could swell and destroy such stamps.

Diazonium resins and salts have also been used for forming multiple layers of enzymes or of polyoxometallates on the surface of various materials by electronic complexation and then. This process remains limited since it requires the existence of electronic interactions between the species intended to be deposited on the surface and the diazo-compounds. In addition, it does not appear to allow grafting with the surface. Moreover, diazonium salts are not very stable compounds and upon exposure to ambient light and/or moderately high temperatures, these materials have been known to dissociate resulting in removal from the surface.

BRIEF SUMMARY

Disclosed herein are sensor devices and processes for manufacturing the sensor devices and detecting a target molecule with the sensor device. In one embodiment, a sensor device comprises a substrate comprising a channel and first and second electrodes electrically connected to the channel, wherein the channel comprises a monolayer of surface functionalized graphene or surface functionalized carbon nanotubes, wherein the surface functionalized graphene or surface functionalized carbon nanotubes comprises an imidazolidone compound.

A process of manufacturing a sensor device comprises overlaying a dielectric layer onto a substrate; depositing graphene or carbon nanotubes onto the dielectric layer; forming a source electrode and a drain electrode on the substrate such that the graphene layer defines a channel therebetween and is electrically connected to the source and drain electrodes; and functionalizing a surface of the graphene with an imidazolidone compound.

In another embodiment, a process for detecting a target molecule with a sensor device comprises providing a sensor device comprising a channel and first and second electrodes electrically connected to the channel, wherein the channel comprises a monolayer of surface functionalized graphene or surface functionalized carbon nanotubes, wherein the surface functionalized graphene or surface functionalized carbon nanotubes comprises an imidazolidone compound; immobilizing probe molecules with the surface functionalized graphene or surface functionalized carbon nanotubes; and binding target molecules to the probe molecules.

Additional features are realized through the techniques of the present exemplary embodiment. Other embodiments are described in detail herein and are considered a part of what is claimed. For a better understanding of the features of the exemplary embodiment, refer to the description and to the drawings.

BRIEF DESCRIPTION OF THE SEVERAL VIEWS OF THE DRAWINGS

Referring now to the drawings wherein like elements are numbered alike in the several FIGURES.

DETAILED DESCRIPTION

Figure 1:
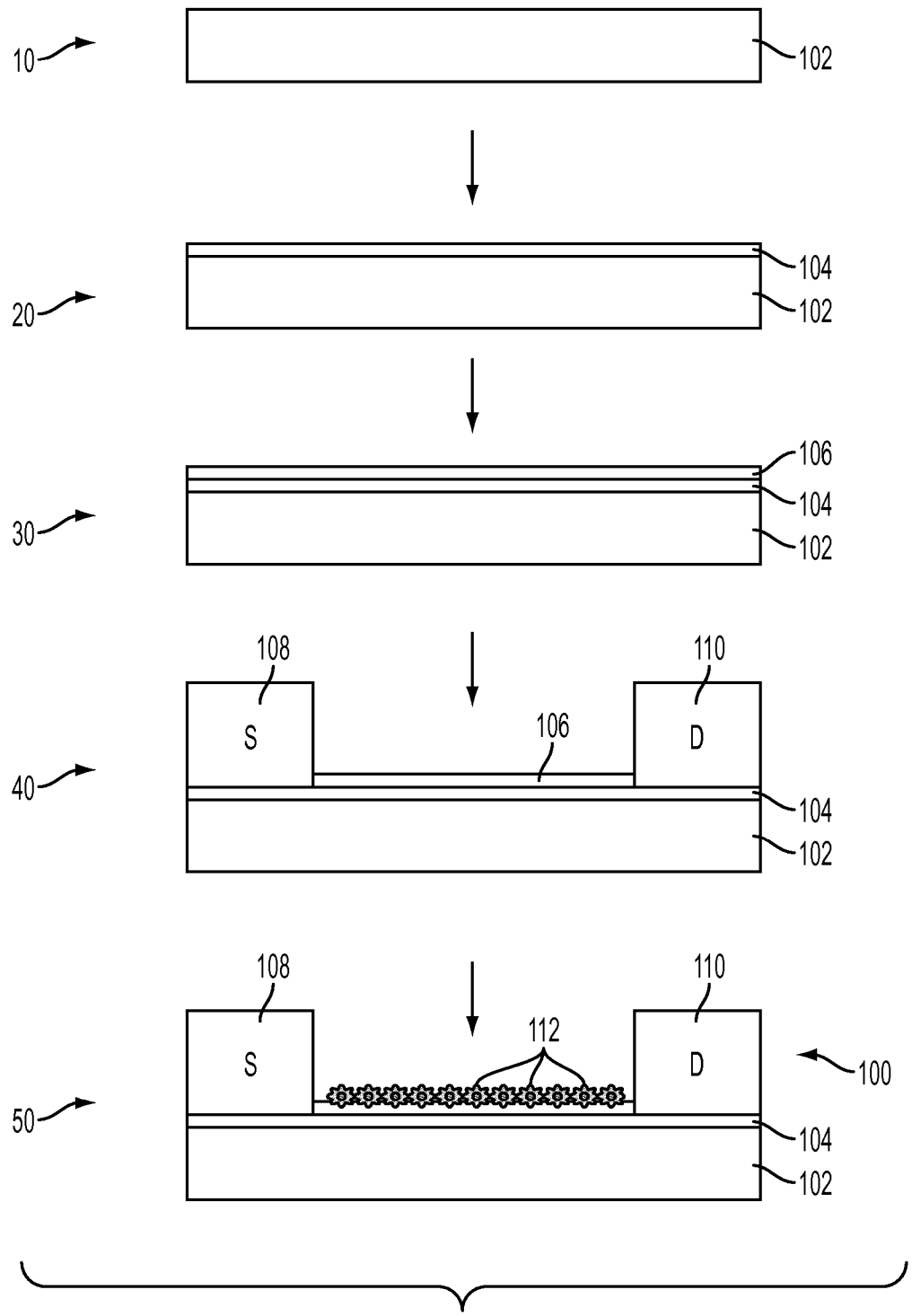
FIG. 1 illustrates an exemplary process of forming a carbon based biosensor device 100 including nanochannels formed of graphene or carbon nanotubes that have a functionalized surface of an imidazolidone compound in accordance with the present disclosure.

The present disclosure is generally directed to carbon based biosensors and processes for the manufacture thereof. The carbon based biosensors generally include a channel surface formed of graphene or carbon nanotubes (CNT) functionalized with an imidazolidone compound. The imidazolidone compound includes an imidazolidone ring for self assembly to the carbon surface, e.g., graphene or CNT, and at least one additional functionality for selective immobilization of a targeted analyte. The imidazolidone compound provides stable bonding to the carbon surface and is relatively small in size, thereby providing the carbon based biosensor with increased sensitivity. Advantageously, the imidazolidone ring itself is stable to radiation and/or heat such as may be encountered during fabrication of the biosensor.

More particularly, the present disclosure relates to field-effect transistor (FET) biosensors and uses thereof, and in particular, to FET-based biosensors using graphene-based sheets or carbon nanotubes that have been surface functionalized with the imidazolidone compound. The present disclosure provides a reliable method to immobilize biomolecules (e.g., antibodies or the like). The immobilization of the biomolecules allows for a more stable attachment of the biomolecules. The more stable attachment provides improved device reliability/repeatability and improved specificity of the sensor.

The term "carbon nanotube (CNT)" is used throughout the present application to include a one-dimensional nanomaterial that has a hollow cavity with nanometer-sized diameters and much, much longer lengths. In other words, the carbon nanotubes have a high aspect ratio and quantum effects become important for these systems. The nanotubes that can be used in the present disclosure are single walled or multi-walled nano-materials that typically have an outer diameter that is typically from about 0.8 nanometers (nm) to about 30 nm, with an outer diameter from about 1.0 nm to about 2.5 nm being more typical, and a length that is typically from about 5 nm to about 100 micrometers (μm), with a length from about 10 nm to about 10 μm being more typical. In addition to having an outer diameter, the nanotubes that can be used in the present disclosure have an inner diameter that is typically from about 0.8 nm to about 15 nm, with an inner diameter from about 0.8 nm to about 2.5 nm being more highly typical. The nanotubes useful in the present disclosure are further characterized as having a high aspect ratio that is typically on the order of about 5 or greater, with an aspect ratio from about 5 to about 5000 being typical.

The carbon nanotubes used in the present disclosure are made using techniques well known to those skilled in the art. For example, the carbon nanotubes can be formed by laser ablation, chemical vapor deposition (CVD) of various organic materials, such as carbon monoxide, methane, and ethanol, and electrical discharge.

The term "graphene" generally refers to a single layer of carbon atoms in a two-dimensional honeycomb lattice. Compared to CNTs, graphene-based sheets generally have a higher carrier mobility and specific surface area, which enhances the sensor performance.

The terms "analyte", "target compound", "target molecule" or "target" as interchangeably used herein, refer to any substance that can be detected in an assay by binding to a binding molecule, and which, in one embodiment, may be present in a sample. Therefore, the analyte can be, without limitation, any substance for which there exists a naturally occurring antibody or for which an antibody can be prepared. The analyte may, for example, be a small organic compound such as a drug, toxin, herbicide, and metabolites thereof, dye, or other small molecule present in the sample. Additionally, however, the analyte may also be an antigen, a protein, a polypeptide, a nucleic acid, a hapten, an immunological hapten, a carbohydrate, a cell or any other of a wide variety of biological or non-biological molecules, complexes or combinations thereof. The analyte may be a protein, peptide, carbohydrate or lipid derived from a biological source such as bacterial, fungal, viral, plant or animal samples. The analyte may be a small molecule, such as a molecule with a molecular weight of below 1 kDa or of below 500 Da. Alternatively or additionally, the analyte may have no net charge and/or no dipole moment or a net charge and/or dipole moment that is too small to allow detection of the analyte in the absence of a suitable carrier.

In one embodiment, the graphene or carbon nanotube surfaces are functionalized with an imidazolidone compound of formula (I):

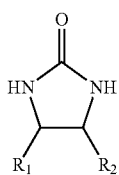

(I)

wherein $R_1$ and $R_2$ are each independently selected from the group consisting of hydrogen, an alkyl group with 1 to 16 carbon atoms, an amine group, an alkylamine group, an aldehyde group and a carboxylic acid and an ester.

In another embodiment, the graphene or carbon nanotube surfaces are functionalized with an imidazolidone compound that is a glycoluril compound of formula (II).

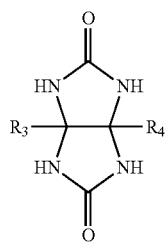

(II)

wherein $R_3$ and $R_4$ are each independently selected from the group consisting of hydrogen, an alkyl group, an aryl group, and mixtures thereof.

FIG. 1 illustrates an exemplary method of forming a carbon based biosensor device 100, e.g., a field effect transistor (FET) having a nanochannels formed of graphene or CNT having a functionalized surface of the imidazolidone compound.

In the manufacture of the biosensor device 100, a substrate 102 is provided in a first step 10. Most biosensor substrates are constructed with silicon. Other suitable materials include, but are not limited to any solid substrates such as glass, metal substrates, and other semiconductor substrates.

In step 20, a gate dielectric layer 104 is then deposited and/or formed on the substrate 102. For silicon substrates, the gate dielectric can be thermally grown silicon dioxide, i.e., $SiO_2$ (also referred to as the "gate oxide"), since the thermally grown oxide has a very clean interface. However, alternative materials with higher dielectric constants can be used, which would allow for higher capacitance at the same thickness. For example, a suitable dielectric material may includes oxides of at least one metal selected from group IVB, VB, VIIB, VIIB, VIII or IIA (CAS version) of the Periodic Table of Elements. By way of example, a suitable gate dielectric material can include, but are not limited to, $Al_2O_3$, $HfO_2$, $TiO_2$, $SnO_2$ or $ZrO_2$. The gate dielectric 102 may be located atop another dielectric material (not shown) or a semiconducting material.

In step 30, a channel layer 106 formed of graphene or carbon nanotubes is then deposited onto the dielectric layer 104.

For example, a layer of graphene can be mechanically exfoliated from natural graphite onto the dielectric surface using known techniques. Alternatively, the graphene can be prepared by chemical vapor deposition processes. After transfer, the graphene layer may be annealed at an elevated temperature for a period of time, e.g., 600° C. in vacuum for 10 minutes.

Similarly, a dispersion of the carbon nanotubes can be applied onto the substrate. In some embodiments, the carbon nanotubes may be selectively placed (e.g., positioned) onto the dielectric layer 104 by functionalization. That is, an organic functionality having a functional group for bonding to the dielectric layer 104 may be formed on the carbon nanotubes. The functionalized carbon nanotubes may then be placed (e.g., precisely positioned) on the dielectric layer 104 by depositing the functionalized carbon nanotubes on the dielectric layer 104 so that the organic functionality bonds to the dielectric material.

The positioning of the functionalized carbon nanotubes may follow the shape and orientation of the bonding surface. In particular, the bonding surface may have a rectangular shape (e.g., L>W) so that when the nanostructure is deposited on the bonding surface, the functionalized carbon nanotubes bond to the bonding surface such that the longitudinal axis of the carbon nanotubes is substantially aligned with the longitudinal direction (i.e., L) of the bonding surface.

After placing the functionalized carbon nanotubes on the bonding surface (i.e., dielectric layer), the organic functionality may be removed from the carbon nanotubes such as by annealing the device. The specific annealing conditions can be varied widely, depending on the specific types of carbon nanotubes used. For nanotubes with an average tube diameter ranging from about 0.8 nm to about 1.2 nm (measured before the functionalization), the annealing temperature may range from about 450° C. to about 650° C., more preferably from about 500° C. to about 600° C., and the annealing duration may range from about 60 seconds to about 120 minutes, and more preferably from about 120 seconds to about 60 minutes. The structural integrity of the nanotubes is maintained during the annealing process.

The substrate 102 may also include a non-bonding surface (not shown) to which the functional group has little potential for bonding (e.g., will not bond). For example, if the carbon nanotubes are functionalized with an organic acid functionality, the bonding surface may include a metal oxide surface and the non-bonding surface may include a silicon oxide surface. In addition, in some embodiments, the non-bonding surface may be formed around a periphery of the bonding surface, from a plane view perspective.

Further, the non-bonding surface may include plural non-bonding surfaces including different types of materials. Further, the non-bonding surface may include substantially the entire uppermost surface of the substrate, except for the portion which includes the bonding surface. That is, in this aspect, the uppermost surface of the substrate includes either the bonding surface or the non-bonding surface. In this case, there is no surface, other than the bonding surface, on the uppermost surface of the substrate to which the functionalized carbon nanotubes will bond.

In order to ensure that the carbon nanotubes are placed such that the longitudinal axis of the nanostructure is formed along the length (L) of the bonding surface, the length (L) should be at least greater than the width (W) of the bonding surface. In an exemplary aspect, the bonding surface may have a width in a range from 10 nm to 500 nm, and a length in a range from 1 μm to 100 μm.

Further, the length (L) and width (W) of the bonding surface may depend to a certain extent on the length ($l_N$) of the carbon nanotubes to be placed on the bonding surface, and the diameter ($d_N$) of the carbon nanotubes. For example, the length (L) should be at least 10 times the length ($l_N$) of the carbon nanotubes, and more preferably, at least 100 times the length ($l_N$) of the carbon nanotubes, and the width (W) should be less than 1000 times the diameter ($d_N$) of the carbon nanotubes and more preferably, less than 100 times the diameter ($d_N$) of the carbon nanotubes, to ensure, for example, that the carbon nanotubes is precisely placed (e.g., longitudinally placed and not transversely placed) on the bonding surface.

In addition, the bonding surface (e.g., metal oxide dielectric layer) should have a sufficient thickness but not be so thick that the carbon nanotubes bonds to the side of the bonding surface and not an upper surface of the bonding surface as intended. Thus, the bonding surface should have a thickness in a range from 1 nm to 100 nanometers.

In step 40, source and drain electrodes 108, 110, respectively, are then formed by photolithography over the substrate surface in direct contact with the channel layer 106 of carbon nanotubes or graphene, so as to form FETs with carbon nanotube or graphene channels. The channel length of the FETs formed by the method of the present disclosure typically ranges from about 50 nm to about 1000 nm, more typically from about 100 nm to about 500 nm, and most typically from about 350 nm to about 450 nm.

In step 50, the channel surface 106 (i.e., the exposed surfaces of the graphene or carbon nanotubes) is functionalized via self assembly with the imidazolidone compound 112 to complete the device 100. A dispersion or solution of the imidazolidone compound is applied to the channel surface. The imidazolidone compound can include an additional functional group specific to the target analyte. For example, when the target analyte is a protein such as streptavidin, the imidazolidone compound can be glycoluril of formula (II), wherein $R_3$ and $R_4$ are hydrogen. As previously discussed, glycoluril includes two condensed imidazolidone rings. One of the imidazolidone rings is used for self assembly onto the graphene or carbon nanotube channel surface and the other imidazolidone ring can be utilized for immobilization probe molecules with biotin for example, which can the bind the streptavidin protein to the sensor.

Figure 2:
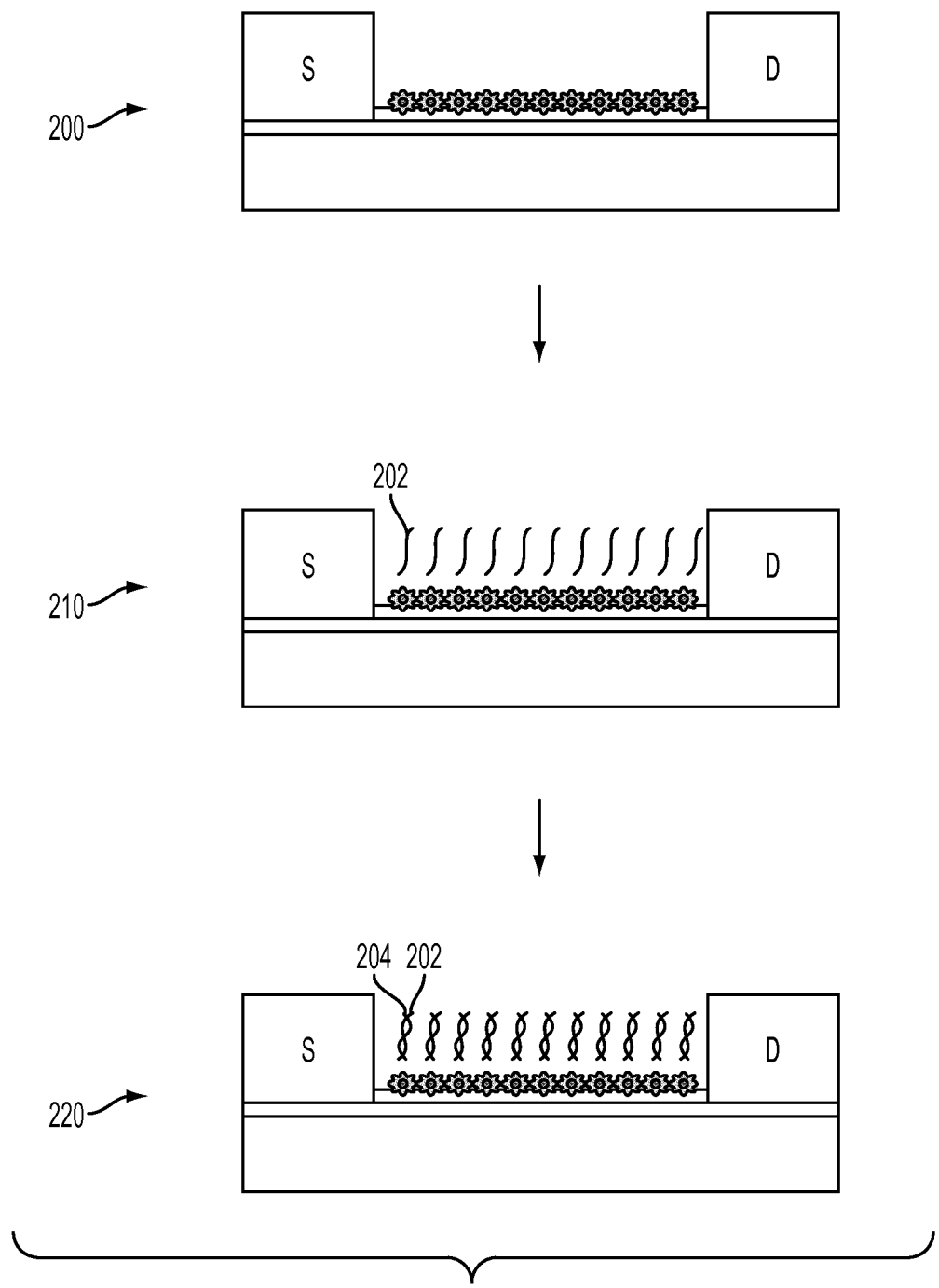
FIG. 2 illustrates an exemplary process flow for immobilizing a target analyte with a sensor device in accordance with the present disclosure.

Referring now to FIG. 2, there is shown an exemplary process flow for immobilizing a target analyte with the device 100. In step 200, the biosensor device such as device 100 is provided.

In step 210, probe molecules 202 are immobilized onto the imidazolidone compound to interface with soluble biologically relevant targets that can localize the target molecule in close vicinity of the channel.

In step 220, the target molecules 204 bind to the probe molecules. The use of the relatively small imidazolidone compound provides a large surface area density and the base for many sensor surfaces operating in parallel, allowing increased electrochemically active area for high sensitivity and high signal intensity. Upon binding of the target molecule to the channel surface, a signal is detected and determined. The signal may be, for example, a change in conductance detected by electrodes connected to the detection area. The determined change in conductance can then be correlated to the presence or amount of the target analyte in a sample.

Optionally, the imidazolidone compound can be used as a seed layer for an atomic layer deposition process on a surface includes CNTs or graphene.

The following examples are provided to illustrate the various processing schemes of the present disclosure for the selective placement of carbon nanotubes.

EXAMPLE 1

Figure 3:
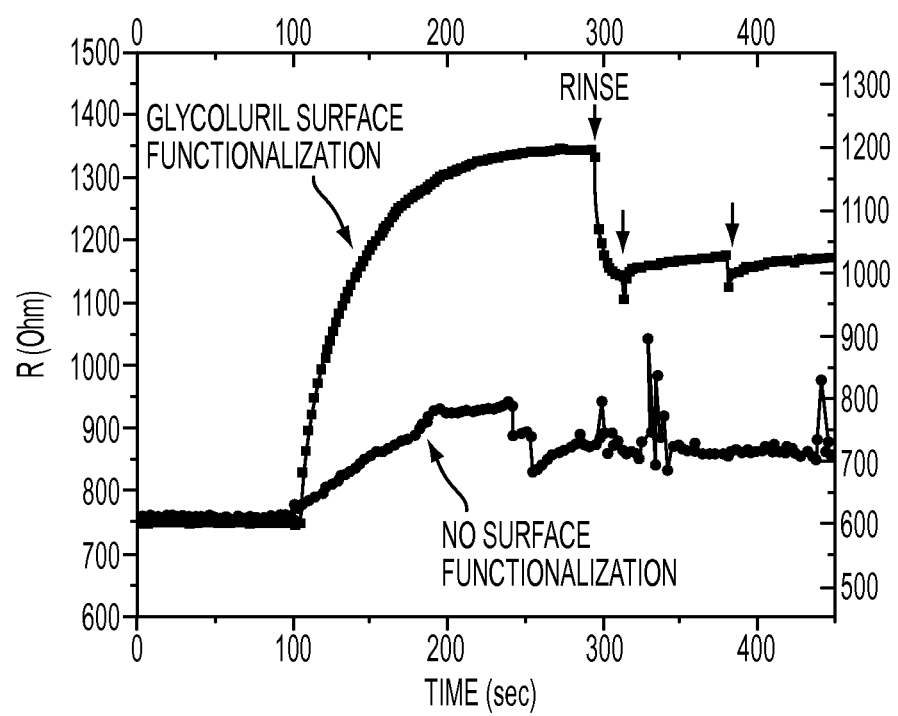
FIG. 3 graphically illustrates the change in resistance as a function of immobilization of the streptavidin.

In this example, a biosensor device including channels formed of glycoluril surface functionalized graphene was compared to a similar biosensor device without the glycoluril surface functionalization provided in the channel. The biosensors were exposed to a solution containing streptavidin as the target analyte and resistance was subsequently measured. FIG. 3 graphically illustrates the change in resistance as a function of immobilization of the streptavidin. The solution containing the streptavidin was introduced after about 100 seconds. As shown, the biosensor including the glycoluril functionalized channel was highly sensitive to target molecule binding as evidenced by the marked change in resistance. Moreover, resistance was relatively stable after periodic rinsing of the biosensor, which infers that glycoluril stable binding affinity to the streptavidin molecules. In comparison, the biosensor including channels without the surface functionalization provided minimal resistance change. The shape of the curve from the non-functionalized sensor also suggests the precipitation of target molecules which is different to the binding reaction that can be seen from the shape of the curve of the functionalized sensor.

In the following description, numerous specific details are set forth, such as particular structures, components, materials, dimensions, processing steps and techniques, in order to provide a thorough understanding of the present disclosure. However, it will be appreciated by one of ordinary skill in the art that the disclosure may be practiced without these specific details. In other instances, well-known structures or processing steps have not been described in detail in order to avoid obscuring the disclosure.

It will be understood that when an element as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A sensor device comprising:
   a substrate comprising a channel and first and second electrodes electrically connected to the channel, wherein the channel comprises a monolayer of surface functionalized graphene or surface functionalized carbon nanotubes, wherein the surface functionalized graphene or surface functionalized carbon nanotubes comprises an imidazolidone compound, wherein the imidazolidone compound is of formula (1):

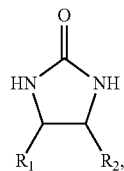

(I)

wherein $R_1$ and $R_2$ are each independently selected from the group consisting of hydrogen, an alkyl group with 1 to 16 carbon atoms, an amine group, an alkylamine group, an aldehyde group and a carboxylic acid and an ester.

2. The sensor device of claim 1, further comprising a dielectric layer intermediate the substrate and the channel.

3. The sensor of claim 2, wherein the substrate comprises silicon and the dielectric layer is a thermally grown silicon dioxide.

4. The sensor device of claim 2, wherein the dielectric layer comprises an oxide of at least one metal selected from group IVB, VB, VIB, VIIB, VIII or IIA (CAS version) of the Periodic Table of Elements.

5. The sensor device of claim 2, wherein the dielectric layer comprises $Al_2O_3$, $HfO_2$, $TiO_2$, $SnO_2$ or $ZrO_2$.

6. The sensor device of claim 1, wherein the channel has a length of about 50 nm to about 1000 nm.

7. The sensor device of claim 1, wherein the carbon nanotubes have an outer diameter from about 0.8 nm to about 30 nm and a length that from about 50 nm to about 100 μm.

8. A sensor device comprising:
   a substrate comprising a channel and first and second electrodes electrically connected to the channel, wherein the channel comprises a monolayer of surface functionalized graphene or surface functionalized carbon nanotubes, wherein the surface functionalized graphene or surface functionalized carbon nanotubes comprises an imidazolidone compound, wherein the imidazolidone compound is of formula (II):

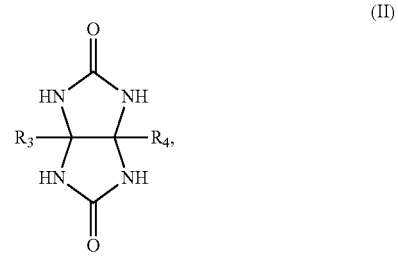

(II)

wherein $R_3$ and $R_4$ are each independently selected from the group consisting of hydrogen, an alkyl group, an aryl group, and mixtures thereof.

9. The sensor device of claim 1, further comprising a dielectric layer intermediate the substrate and the channel.

10. The sensor of claim 9, wherein the substrate comprises silicon and the dielectric layer is a thermally grown silicon dioxide.

11. The sensor device of claim 9, wherein the dielectric layer comprises an oxide of at least one metal selected from group IVB, VB, VIB, VIIB, VIII or IIA (CAS version) of the Periodic Table of Elements.

12. The sensor device of claim 9, wherein the dielectric layer comprises $Al_2O_3$, $HfO_2$, $TiO_2$, $SnO_2$ or $ZrO_2$.

13. The sensor device of claim 8, wherein the channel has a length of about 50 nm to about 1000 nm.

14. The sensor device of claim 8, wherein the carbon nanotubes have an outer diameter from about 0.8 nm to about 30 nm and a length that from about 5 nm to about 100 μm.

* * * * *